(12) United States Patent
Eastwood et al.

(10) Patent No.: US 8,354,069 B2
(45) Date of Patent: Jan. 15, 2013

(54) PLUG FLOW SYSTEM FOR IDENTIFICATION AND AUTHENTICATION OF MARKERS

(75) Inventors: Ian Eastwood, Rossendale Lancs (GB); Erwin Dorland, York (GB); Andrew Taylor, Leeds (GB)

(73) Assignee: Authentix, Inc., Addison, TX (US)

( * ) Notice: Subject to any disclaimer, the term of this patent is extended or adjusted under 35 U.S.C. 154(b) by 657 days.

(21) Appl. No.: 12/182,749

(22) Filed: Jul. 30, 2008

(65) Prior Publication Data

US 2009/0023223 A1   Jan. 22, 2009

Related U.S. Application Data

(63) Continuation-in-part of application No. PCT/US2006/008217, filed on Mar. 8, 2006.

(60) Provisional application No. 60/659,669, filed on Mar. 8, 2005.

(51) Int. Cl.
*B01J 19/00* (2006.01)
*G01N 15/06* (2006.01)
*G01N 33/00* (2006.01)

(52) U.S. Cl. ....... 422/224; 205/687; 422/68.1; 422/129; 436/172; 436/177

(58) Field of Classification Search .................. None
See application file for complete search history.

(56) References Cited

U.S. PATENT DOCUMENTS

| | | | |
|---|---|---|---|
| 3,773,753 A | 11/1973 | Wright et al. | |
| 3,822,999 A | 7/1974 | Pope | |
| 4,011,284 A | 3/1977 | Gawne et al. | |
| 4,049,638 A | 9/1977 | Doerfel et al. | |
| 4,097,361 A | 6/1978 | Ashworth | |
| 4,140,373 A | 2/1979 | Rull | |
| 4,244,061 A | 1/1981 | Webster et al. | |
| 4,330,508 A | 5/1982 | Weir et al. | |

(Continued)

FOREIGN PATENT DOCUMENTS

| DE | 295 18 840 | 1/1996 |
|---|---|---|
| EP | 0 278 755 | 8/1988 |
| EP | 0 233 696 | 12/1990 |

(Continued)

OTHER PUBLICATIONS

FLLEX—Flow Liquid/Liquid Extraction, "How does the FLLEX work?" (2 pages) [Online], [Retrieved from the Internet on Jun. 27, 2008]. Retrieved from the Internet: <URL: http://www.syrris.com/How-Does-The FLLEX-work.aspx>.

(Continued)

*Primary Examiner* — Krishnan S Menon
*Assistant Examiner* — Dirk Bass
(74) *Attorney, Agent, or Firm* — Kelly Kordzik; Matheson Keys Garsson & Kordzik PLLC

(57) ABSTRACT

Devices and methods for extraction, identification, authentication, and quantification of one or more covert markers in a material are disclosed. An extraction system includes a first plug flow mixer for mixing a first fluid bearing a marker and transfer agent into a plug flow. The mixing and flowing of the immiscible liquids causes transfer of the marker from the fluid to the transfer agent. A splitter having filters of different surface energies separates the two immiscible liquids, the transfer agent bearing the marker. A second plug flow can be used to transfer the marker to a second transfer agent. The transferred marker is detected to authenticate the original fluid. The marker can be further isolated, activated, or reacted to perform detection, identification or authentication. With the device, a number of independent processing and analytic steps are combined onto a single, portable unit.

24 Claims, 11 Drawing Sheets

U.S. PATENT DOCUMENTS

| | | | |
|---|---|---|---|
| 4,360,662 A | 11/1982 | Williams |
| 4,374,808 A | 2/1983 | Weir et al. |
| 4,376,693 A | 3/1983 | Warzel |
| 4,397,100 A | 8/1983 | Dickey et al. |
| 4,402,832 A | 9/1983 | Gerhold |
| 4,413,058 A | 11/1983 | Arcuri et al. |
| 4,478,721 A | 10/1984 | Gerhold |
| 4,484,012 A | 11/1984 | Stahl et al. |
| 4,498,991 A | 2/1985 | Oroskar |
| 4,508,745 A | 4/1985 | Fulger et al. |
| 4,533,743 A | 8/1985 | Medeiros et al. |
| 4,544,567 A | 10/1985 | Gottesman |
| 4,633,893 A | 1/1987 | McConnell et al. |
| 4,721,575 A | 1/1988 | Binning et al. |
| 4,799,504 A | 1/1989 | Scragg et al. |
| 4,809,934 A | 3/1989 | Rix |
| 4,891,318 A | 1/1990 | Oosterhuis et al. |
| 4,908,099 A | 3/1990 | DeLong |
| 4,960,513 A | 10/1990 | Young |
| 4,999,102 A | 3/1991 | Cox et al. |
| 5,064,623 A | 11/1991 | Harandi et al. |
| 5,069,925 A | 12/1991 | Lee et al. |
| 5,078,901 A | 1/1992 | Sparrow |
| 5,180,503 A | 1/1993 | Gorelick et al. |
| 5,232,475 A | 8/1993 | Jepson |
| 5,244,550 A | 9/1993 | Inoue |
| 5,250,104 A | 10/1993 | Berger et al. |
| 5,268,103 A | 12/1993 | Jameson et al. |
| 5,288,169 A | 2/1994 | Neeper |
| 5,358,357 A | 10/1994 | Mancini et al. |
| 5,389,267 A | 2/1995 | Gorelick et al. |
| 5,453,285 A | 9/1995 | Versteegh |
| 5,464,309 A | 11/1995 | Mancini et al. |
| 5,525,235 A | 6/1996 | Chen et al. |
| 5,525,516 A | 6/1996 | Krutak et al. |
| 5,578,209 A | 11/1996 | Weiss |
| 5,601,707 A | 2/1997 | Clay et al. |
| 5,637,766 A | 6/1997 | Hsu et al. |
| 5,655,852 A | 8/1997 | Duffney et al. |
| 5,679,258 A | 10/1997 | Petersen |
| 5,709,505 A | 1/1998 | Williams et al. |
| 5,772,775 A | 6/1998 | Riviere |
| 5,879,543 A | 3/1999 | Amini |
| 5,885,460 A | 3/1999 | Dague et al. |
| 5,905,171 A | 5/1999 | Hsu |
| 5,932,091 A | 8/1999 | Tompkins et al. |
| 5,976,336 A | 11/1999 | Dubrow et al. |
| 5,997,929 A | 12/1999 | Heeb et al. |
| 6,017,383 A | 1/2000 | Jepson |
| 6,031,138 A | 2/2000 | Hsu et al. |
| 6,058,623 A | 5/2000 | Brooks et al. |
| 6,068,752 A | 5/2000 | Dubrow et al. |
| 6,099,742 A | 8/2000 | Komistek |
| 6,117,334 A | 9/2000 | Coury et al. |
| 6,153,073 A | 11/2000 | Dubrow et al. |
| 6,156,197 A | 12/2000 | Dessapt |
| 6,235,175 B1 | 5/2001 | Dubrow et al. |
| 6,251,615 B1 | 6/2001 | Oberhardt |
| 6,297,061 B1 | 10/2001 | Wu et al. |
| 6,310,106 B1 | 10/2001 | Podubrin et al. |
| 6,350,354 B1 | 2/2002 | Neuman et al. |
| 6,399,131 B2 | 6/2002 | Zeller et al. |
| 6,402,959 B1 | 6/2002 | Dessapt et al. |
| 6,436,290 B1 | 8/2002 | Glassford |
| 6,454,944 B1 | 9/2002 | Raven |
| 6,572,784 B1 | 6/2003 | Coombs et al. |
| 6,930,778 B2 | 8/2005 | Yamaguchi et al. |
| 6,936,110 B2 | 8/2005 | Thorre |
| 7,101,467 B2 | 9/2006 | Spaid |
| 7,172,688 B2 | 2/2007 | Petersen |
| 7,374,668 B1 | 5/2008 | DiValentin et al. |
| 2002/0028471 A1 | 3/2002 | Oberhardt |
| 2003/0145894 A1 | 8/2003 | Burns et al. |
| 2003/0178075 A1 | 9/2003 | Moon et al. |
| 2003/0230486 A1 | 12/2003 | Chien et al. |
| 2004/0071597 A1 | 4/2004 | Hattori et al. |
| 2004/0072278 A1 | 4/2004 | Chou et al. |
| 2004/0188254 A1 | 9/2004 | Spaid |
| 2004/0219078 A1 | 11/2004 | Kitamori et al. |
| 2004/0224380 A1 | 11/2004 | Chou et al. |
| 2004/0225249 A1 | 11/2004 | Leonard |
| 2004/0229349 A1 | 11/2004 | Daridon |
| 2004/0233449 A1 | 11/2004 | Yamaguchi et al. |
| 2004/0256321 A1 | 12/2004 | Goldsmith |
| 2004/0257575 A1 | 12/2004 | Yamaguchi et al. |
| 2004/0263335 A1 | 12/2004 | Molnar |
| 2005/0042449 A1 | 2/2005 | Phillips |
| 2005/0060171 A1 | 3/2005 | Molnar |
| 2005/0121375 A1 | 6/2005 | Petersen |
| 2005/0140971 A1 | 6/2005 | Yamaguchi et al. |
| 2005/0142624 A1 | 6/2005 | Kitamori et al. |
| 2005/0158213 A1 | 7/2005 | Tsudome et al. |
| 2005/0260764 A1 | 11/2005 | Grisby et al. |
| 2005/0263398 A1 | 12/2005 | Tsudome et al. |
| 2006/0070956 A1 | 4/2006 | Herrmann |
| 2006/0210689 A1 | 9/2006 | Velissariou et al. |
| 2007/0033863 A1 | 2/2007 | Butler et al. |
| 2007/0151852 A1 | 7/2007 | Chien et al. |
| 2007/0221538 A1 | 9/2007 | D'Alessandro et al. |

FOREIGN PATENT DOCUMENTS

| | | |
|---|---|---|
| EP | 0 847 601 | 1/2000 |
| GB | 2 241 443 | 9/1991 |
| GB | 2 355 211 | 4/2001 |
| JP | 63270508 | 11/1988 |
| JP | 02035337 | 2/1990 |
| JP | 02098582 | 4/1990 |
| JP | 03262502 | 11/1991 |
| JP | 04130182 | 5/1992 |
| JP | 04215807 | 8/1992 |
| JP | 06193564 | 7/1994 |
| JP | 06226006 | 8/1994 |
| JP | 06226007 | 8/1994 |
| JP | 08196809 | 8/1996 |
| JP | 09174049 | 7/1997 |
| JP | 09206504 | 8/1997 |
| JP | 00042542 | 2/2000 |
| JP | 01133450 | 5/2001 |
| JP | 02233705 | 8/2002 |
| WO | WO 96/09103 | 3/1996 |
| WO | WO 98/45929 | 10/1998 |
| WO | WO 02/01044 | 1/2002 |
| WO | WO 03/082429 | 10/2003 |
| WO | WO 2005/028066 | 3/2005 |
| WO | WO 2006/096761 | 9/2006 |
| WO | WO 2007/054392 | 5/2007 |
| WO | WO 2007/120684 | 10/2007 |
| WO | WO 2007/137245 | 11/2007 |

OTHER PUBLICATIONS

Taylor, G., "Dispersion of Soluble Matter in Solvent Flowing Slowly Through a Tube," Proceedings of the Royal Society of London. Series A, Mathematical and Physical Sciences, vol. 219, No. 1137. Aug. 25, 1953, pp. 186-203. Published by The Royal Society, London, GB.

Kashid, et al., "On the hydrodynamics of liquid-liquid slug flow capillary microreactors," Asia-Pacific Journal of Chemical Engineering, vol. 3, Issue 2, pp. 151-160. Published Online Jun. 25, 2008 by Curtin University of Technology, Western Australia with John Wiley, United Kindom. [Online], [retrieved on Jun. 27, 2008]; Retrieved from the Internet: <URL: http://www.google.com/search?q=cache:qfLnc0FYaPMJ:www.mathematik.uni-dortmund.de/Isiii/static/showpdffile_KashidRivasAgarTurek2007.pdf+slug+flow+liquid-liquid&hl=en&ct=clnk&ed=3&gl=us> (26 pages).

Kashid, et al., "Liquid-Liquid Slug Flow in a Capillary: An Alternative to Suspended Drop or Film Contactors," (2 pages) [Online], [Retrieved on Sep. 9, 2008]. Retrieved from the Internet: <URL: http://www.ncl-india.org/camure/upload/cam78Abstract-CAMURE-ISMR-07-Kashid-Harshe-Agar.pdf>.

Tokeshi, et al., "Continuous-Flow Chemical Processing on a Microchip by Combining Microunit Operations and a Multiphase Flow Network," Analytical Chemistry, vol. 74, No. 7, Apr. 1, 2002, pp. 1565-1571.

International Search Report and Written Opinion, PCT/US2009/052069, Apr. 9, 2010.

PLUG FLOW SYSTEM FOR IDENTIFICATION AND AUTHENTICATION OF MARKERS

RELATED APPLICATIONS

This application is a continuation-in-part of, and claims priority under 35 U.S.C. 365(a) from, International Application No. PCT/US2006/008217, filed Mar. 8, 2006, which claims priority from U.S. Provisional Patent Application Ser. No. 60/659,669, filed Mar. 8, 2005. Both priority applications are incorporated herein in their entirety.

BACKGROUND

1. Technical Field

The present invention relates generally to the field of identification and authentication. More particularly, the present invention relates to methods and devices for identification, quantification, and authentication of one or more materials, especially those containing one or more covert or latent markers.

2. Background

Identification and authentication of solid, liquid and gaseous materials may use many techniques, including the use of overt or covert features or additives, such as colorants and dyes, e.g., tracers or markers. The overt or covert features or additives are typically used to identify, detect, authenticate, and distinguish a product or manufacturer's material from others and to prevent misuse, adulteration, counterfeiting, and/or imitations of the material. While overt additives or features are readily identifiable, covert additives and features are not. In many cases, covert additives or features require that the additive or feature be isolated from the material in order to better identify, quantify, and/or authenticate.

Conventional techniques for isolating and identifying an additive or feature from a material often require highly trained personnel to perform a series of complicated steps using a number of different laboratory tools and/or machines. The steps may include, without limitation, processing, extraction, separation, identification, and quantification, where each step typically requires its own set of machines and tools, and subsequently, its own set of errors and waste products.

For example, costly laboratory studies based on X-ray fluorescence or GC Mass spectroscopy generally provide highly accurate results but with considerable cost and delay. One proposed field testing technology is based on antibodies used to identify markers. This technique has a benefit of sensitivity and selectivity of the antibodies to a specific marker. The antibody method, however, can be expensive, and the system requires manual handling of the sample by highly trained personnel.

Among other limitations, current technologies limit rapid identification and quantification of a covert additive or feature. In addition, many of the machines and tools are bulky and not available outside of a laboratory setting, making it difficult to perform any type of identification, quantification, or authentication in situ. Further, there is an increased risk of handling and contamination and the burden of additive waste products. Some existing methods for separating immiscible liquids, e.g., oil and water, often rely on gravity and are generally time consuming and suffer from cross-contamination, particularly if the liquids are in an emulsion. Others rely on use of a centrifuge to separate immiscible liquids. As such, current practice for the identification and authentication of one or more covert markers in a material may be time consuming, error-prone, and expensive.

SUMMARY

The present disclosure provides, among other techniques, methods and systems for identifying, authenticating, and quantifying one or more materials, and in some embodiments, materials including covert features and/or additives.

One aspect of the invention features a system including a plug flow mixer having a first fluid inlet for receiving a fluid containing a marker, a second fluid inlet for receiving a transfer agent and an outlet for conveying a plug flow of the fluid and transfer agent. The plug flow mixer and outlet are configured to permit transfer of the marker from the fluid to the transfer agent. The system further includes a splitter having first and second filters for separating the fluid and the transfer agent bearing the marker from the plug flow.

In some embodiments, the system includes a second plug flow mixer having an inlet for receiving the first transfer agent bearing the marker and a second inlet for receiving a second transfer agent, and an outlet for conveying a plug flow of the first and second transfer agents, wherein the mixer and outlet are configured to permit transfer of the marker from the first transfer agent to the second transfer agent.

In some embodiments a detector is in communication with a splitter outlet for detecting the presence of the marker in the transfer agent.

In some embodiments, the splitter includes a first filter and a second filter with the filters configured respectively to selectively pass one of the fluid and transfer agent and to substantially block the other of the fluid and the transfer agent.

In some cases, the first filter is a lipophobic membrane and the second filter is a hydrophobic membrane.

In some embodiments, the first and second filters are spaced apart a distance approximately equal to the diameter of the outlet of the plug flow mixer, such that plugs conveyed from the outlet are in contact with both the first and the second filter within the splitter.

In some embodiments the splitter further includes a splitter inlet for receiving a plug flow into a filter chamber defined in part by the first and second filters, a first outlet chamber and first outlet for conveying the fluid passed by the first filter, and a second outlet chamber and second outlet for conveying the transfer agent passed by the second filter.

In some embodiments, one of the first and second outlet chamber outlets is positioned diametrically opposite the splitter inlet.

In some embodiments, one of the first and second outlet chambers is tapered in height or width between the inlet and the outlet.

In some embodiments, the filter channel and first and second outlet channels are configured as an ellipse between the splitter inlet and the outlet chamber outlets.

In a particular embodiment, the inlet chamber has a diameter of between 5-10 mm, a height of between 200-400 μm and the outlet chambers each have a diameter of between 5-10 mm and a height of between 100-400 μm.

In some embodiments, one of the first and second outlet chambers defines a network of channels for conveying one of the fluid and the transfer agent to a respective one of the chamber outlets.

In some instances, the fluid comprises a fuel, a lubricant, spirits, or a liquid pharmaceutical.

In some embodiments, the plug flow mixer is in a form of a T-junction or Y-junction.

In some embodiments, the system further includes a data collector, data input device, data analyzer, data storage device, data output device, data retrieval device, or combinations thereof.

In some embodiments, the liquid transfer system is operably coupled to at least one pump driver configured to provide components to the microfluidic device.

In some embodiments, the electromagnetic radiation source is an ultraviolet source, a visible light source, an infrared light source, or a combination thereof.

In some embodiments, the microfluidic cell further includes an upper portion, a lower portion, and at least one channel coupled to the at least one inlet for receiving the material and agent.

Another aspect of the invention features a device configured for single or double extraction of a marker by pH switching or extraction of the marker into a clean solvent whereby it can be detected directly. Extraction is performed using a plug flow of a first liquid bearing a marker and a transfer agent to which the marker is transferred through interaction of the liquids in the plug flow.

In some cases, a second plug flow formed from the first transfer agent carrying the transferred marker and a second transfer agent is used to render the marker more amenable to accurate detection. Use of a clean solvent also reduces the effect of quenching.

Another aspect of the invention features a plug flow splitter having two membrane filters of different surface energies for separating two immiscible liquids. The filters can be arranged in parallel or series.

In some cases, the filters are configured in a close parallel arrangement for continuous fluid separation with reduced cross contamination of the filtered liquids. In some cases, the filters and plug flow systems are compactly arranged to minimize weight and dead space within the system.

Another aspect of the invention features a method of extracting a marker from a fluid. The method includes providing a fluid bearing an overt marker to a first inlet of a plug flow mixer, providing a first transfer agent to a second inlet of a plug flow mixer, and mixing the fluid and the transfer agent in the plug flow mixer to provide a plug flow of the fluid and the transfer agent. The mixing and flowing of the plug flow transfers the marker from the fluid to the transfer agent. The method further includes separating the plug flow into a stream of the transfer agent bearing the marker and a stream of the fluid.

In some applications, the method includes providing a portable microfluidic cell for authenticating a fluid, the microfluidic cell comprising a plurality of channels and providing the transfer agent bearing the marker to a first inlet coupled to the plurality of channels of the microfluidic cell. The method further includes providing a second transfer agent to a second inlet coupled to the plurality of channels of the microfluidic cell, transferring the markers from the first transfer agent to the second transfer agent, and removing at least one of the first and second transfer agents through an outlet of the microfluidic cell to substantially isolate the marker in the microfluidic cell. The method includes identifying or quantifying the marker for authenticating the fluid.

In some applications, the method includes detecting the marker to authenticate the fluid.

In a particular application, detecting the marker includes illuminating the marker with an electromagnetic radiation source.

In some applications, the method includes separating the marker from the transfer agent.

In some applications, providing a fluid includes providing a fuel, a lubricant, spirits, or a liquid pharmaceutical to the first inlet.

In some applications, the method further includes transforming the marker to an activated marker using the transfer agent.

In particular applications, transforming the latent markers includes hydrolysis, oxidation, reduction, structural modification, ionization, electrolysis, complexation, or a combination thereof.

Another aspect of the invention features a program storage device readable by a machine, tangibly embodying a program of instructions executable by the machine to perform the method of extracting a marker from a fluid.

In some applications, the marker is extracted into a second transfer agent. In some cases, the transfer agents are aqueous solutions, organic solutions, water, clean solvent, or other suitable transfer agent.

In some applications, the transfer agent is selected to activate a characteristic of the marker, e.g., by fluorescing, or otherwise reacting with the marker. In some applications, the plug flow and flow separation steps are performed at ambient temperature and relatively low pressure, compared to the extremes of laboratory pump separation and centrifugal separation techniques.

In some applications, extraction is carried out by means of plug flow also known as slug flow or segmented flow. The extractor device contains a pump, phase splitter, series of valves and sensor to provide laboratory type results with a portable field device.

In a particular application, authentication is performed using about 2 ml of fuel and as little as 1.0 ml, 0.5 ml, 0.25 ml or even 0.10 ml of fuel per test.

In one aspect, a system is provided. The system may include one or more of the following components: a microfluidic cell for authenticating a fluid, a liquid transfer system, and/or a detector. The microfluidic cell may include a plurality of channels and a first inlet coupled to the plurality of channels for receiving a fluid comprising markers. The fluid may include, without limitation, a fuel, a lubricant, spirits, or liquid pharmaceuticals. A second inlet may be coupled to the plurality of channels, and may be configured to receive an agent for transferring the markers through the microfluidic cell. Alternatively, or in addition, the agent may be configured to transfer markers in the fluid (e.g., physically or chemically altering the markers) into a form such that the markers may be optically detected. The microfluidic cell may also include an outlet coupled to a channel. The outlet may be configured to remove the fluid, leaving behind the markers.

In other aspects, the microfluidic cell may include a plurality of channels for providing a laminar flow through the microfluidic cell. For example, a first channel may transport a fluid including markers and a second channel may transport a first agent for transferring the markers. The microfluidic cell may also include an outlet for removing liquids within the microfluidic cell. For example, the outlet may be coupled to one of the plurality of channels and may be configured to remove the fluid, leaving markers in the microfluidic cell. The microfluidic cell may also include inlets for receiving liquids, including the fluid including the markers and/or agents.

The microfluidic cell may include a mixer coupled to the plurality of channels. The mixer may be configured to mix components in the channels to yield a mixture. That mixture may be transported via a third channel, where detection can occur.

The liquid transfer system, which may be coupled to the microfluidic cell, may be configured to provide the fluid to the microfluidic cell. In one aspect, the liquid transfer system may include a microscale pump system. Alternatively, or in addition, the liquid transfer system may include a syringe driver or other suitable pumps, including, without limitation, a single charge pump, plunger or piston pump, circumferential pump, diaphragm and bellow pump, gear pump, lobed pump, flexible-vane pump, nutating pump, peristatic pump, volute and diffuser pump, propeller and mixed flow pump, peripheral pump, a syringe, and/or an injector.

The detector, which may be coupled to the microfluidic cell, may be used, among other functions, to identify the markers of the microfluidic cell. In one aspect, the detector may include an electromagnetic radiation source for illuminating the markers.

The detector may also include a sensor configured to collect emissions from the markers.

The detector may also include other components including, without limitation, a data collector, a data input device, a data storage device, a data output device, a data retrieval device, or any combinations thereof.

In other aspects, a method is provided. The method may include the step of providing a microfluidic cell. The microfluidic cell may include, among other components, a plurality of channels. Next, the method may provide a fluid comprising markers to a first inlet coupled to the plurality of channels. An agent may also be provided to the microfluidic cell via, for example, a second inlet. The markers of the fluid are transferred through the microfluidic cell, and may subsequently be transformed by the agent into activated markers. In one embodiment, the markers may be transformed via hydrolysis, reduction, oxidation, structural modification, ionization, electrolysis, complexation, or a combination of the above techniques. The method may also provide removing the fluid through an outlet of the microfluidic cell, where the outlet may be coupled to the plurality of channels. The removal of the fluid may leave substantially the markers and agent in the microfluidic cell.

Next, the method may identify and quantify the markers. In one embodiment, the method may provide steps for illuminating the markers with an electromagnetic radiation source operating in the visible, infrared, and/or ultraviolet spectrum. The method may also provide a sensor to collect emissions from the markers. In some embodiments, the method may provide one or more agents to the microfluidic cell. A first agent may be provided with a fluid including markers to produce a first laminar flow. A second agent may be provided after the fluid is removed from the microfluidic cell, where the first agent and second agent provide a second laminar flow. The method may provide steps for mixing the first and second agents with the markers, yielding a mixture comprising transformed markers. The optical characteristics of the transformed markers may be subsequently detected and the authenticity of the fluid may be determined.

The term "marker" as defined and used in this disclosure refers to a substance that may be detected, such as, but not limited to, linear or non-linear phosphors, organic or inorganic phosphors, or other suitable materials that can exhibit optical characteristics when excited by a light source.

In some embodiments, a marker may be a particle, a microparticle, or a nanoparticle, or the like. In other embodiments, a marker may be a substance that may be encapsulated into for example, a particle, a microparticle, or a nanoparticle. Alternatively, the marker may be a substance that may be dissolved in a material. The term "features," "additives" or the like, as defined and used in this disclosure, typically refer to markers and may be used interchangeably throughout the disclosure.

The terms "covert marker" and "latent marker," as defined and used in this disclosure, refer to markers that are not visibly perceptible by the naked eye. The terms may be used interchangeably throughout the disclosure.

The terms "transformed marker" or "activated marker," as defined and used in this disclosure, refer to markers that can be detected based on its optical characteristics. The terms may be used interchangeably throughout the disclosure.

The term "transferred marker," as defined and used in this disclosure, refers to displacing a marker through a microfluidic cell. In one aspect, a marker may be transferred from one liquid to another liquid. Alternatively, a marker may be transferred from one latent flow to another latent flow.

The term "material," as defined and used in this disclosure, refers to a solid or a liquid material to be authenticated.

The terms "a" and "an" are defined as one or more unless this disclosure explicitly requires otherwise. The terms "substantially," "about," and variations thereof are defined as being largely but not necessarily wholly what is specified as understood by one of ordinary skill in the art, and in one non-limiting embodiment, "substantially" refers to ranges within 10%, 5%, 1%, or 0.5% of what is specified. The term "coupled" is defined as connected, although not necessarily directly, and not necessarily mechanically.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Like reference symbols in the various drawings indicate like elements.

DETAILED DESCRIPTION

Figure 1:
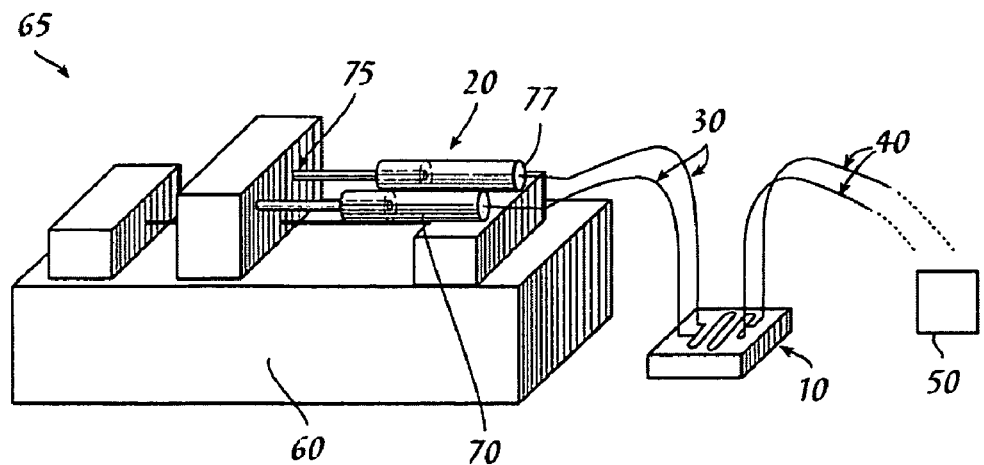
FIG. 1 shows a system for identifying, quantifying, and authenticating a material in accordance with embodiments of this disclosure.

The disclosure and the various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

In the description that follows, like parts may be identified throughout the disclosure and drawings with the same reference numerals, respectively. The drawings are not necessarily to scale and certain features may be shown exaggerated in scale or in somewhat generalized in schematic form in the interest of clarity and conciseness.

The present disclosure provides a single integrated unit that may be used in-line, or in situ, and configured to perform a number of complex laboratory processes, such as, but not limited to, sampling, data analysis and reporting. In one aspect, the present disclosure provides micro-fabrication techniques that allow data analysis to be performed on a micro-scale level. Examples of these technologies include, without limitation, lab-on-a-chip (LOC), micro-total analysis systems (μ-TAS), and micro-electromechanical systems (MEMS). These technologies enable devices produced to be lighter, smaller, and more robust than their laboratory-scale counterparts. Additionally, the device and techniques of the present disclosure increases the speed of diffusion due to, among others things, the geometry of device and the characteristics of a material flowing through the channel.

System for Identifying and Quantifying Markers to Authenticate a Material

Referring to FIG. 1, a system for authenticating a material according to one aspect of the present disclosure is shown. System 65 may include microfluidic cell 10 coupled to at least one liquid transfer system 20 by at least one inlet 30. Liquid transfer system 20 may be housed with driver 60 that operates, in part, to actuate the at least one liquid transfer system 20. Liquid transfer system 20 may be coupled to a fluid holding body 70 that holds one or more liquids. Additional fluid reservoirs (not shown) may also function with liquid transfer system 20. In one aspect, driver 60 may deliver the one or more liquids into fluid holding body 70 via driving block 75 used to push the one or more liquids from fluid holding body 70 to inlet 30 via exit port 77. In some embodiments, driver 60 may deliver liquid at a number of different flow rates and may deliver liquid simultaneously to one or more pumps.

In some embodiments, liquid transfer system 20 may include a microscale or a macroscale pump for providing fluids to microfluidic cell 10. Liquid transfer system 20 may include a mechanically actuated pump. Alternatively, in some embodiments, liquid transfer system 20 may include a manually actuated pump. More generally, liquid transfer system 20 may be a positive-displacement (either bulk-handling or metering pumps) or a non-positive-displacement (centrifugal) system for transferring fluids. Examples of pumps that may be used in a liquid transfer system 20 may include, without limitation, a single charge pump, plunger or piston pump, circumferential pump, diaphragm and bellow pump, gear pump, lobed pump, flexible-vane pump, nutating pump, peristatic pump, volute and diffuser pump, propeller and mixed flow pump, peripheral pump, a syringe, and/or an injector. It is noted that when more than one pump are assembled all of them do not have to be operational, i.e., one or more of the pumps may be inactive.

The at least one inlet 30 may introduce one or more liquids to portions of microfluidic cell 10. In some embodiments, inlet 30 may introduce only one liquid to microfluidic cell 10. Alternatively, inlet 30 may provide more than one liquid to microfluidic cell 10. When more than one liquid is introduced, the fluids may be provided by only one inlet (e.g., when the inlet has a bifurcation prior to entry into microfluidic cell 10) or alternatively, via more than one inlet. The one or more liquids may subsequently be removed by one or more outlets 40 that may be coupled to at least one detection component 50. Inlet(s) 30 and outlet(s) 40 may include tubings (e.g., capillaries or other suitable passageways) that may be configured to move liquid. The tubings may be continuous or may interface with connectors and/or additional tubings, e.g., for introducing additional components, such as a fluid reservoir (not shown) and/or another pump or pump system. The tubings and connectors may be resistant to most chemicals and are, in portable embodiments, typically capillary size. When more than one inlet and/or one or more outlets are assembled, not all inlets and/or outlets have to be operational. One or more inlets and/or one or more outlets may be inactive or blocked.

System 65 may be coupled to a processor. In some embodiments, data from detector 50 may be sent to the processor. In other embodiments, the processor may provide instructions to system 65 and may control the functionalities of the system. The processor may be any computer-readable media known in the art. For example, it may be embodied internally or externally on a hard drive, ASIC, CD drive, DVD drive, tape drive, floppy drive, network drive, flash drive, USB drive, or the like. The processor is meant to indicate any computing device capable of executing instructions for receiving the data from detector 50 amongst other functions. In one embodiment, the processor is a personal computer (e.g., a typical desktop or laptop computer operated by a user). In another embodiment, the processor may be a personal digital assistant (PDA) or other handheld computing device.

In some embodiments, the processor may be a networked device and may constitute a terminal device running software from a remote server, wired or wirelessly. Input from a user, detector, or other system components, may be gathered through one or more known techniques such as a keyboard and/or mouse. Output, if necessary, may be achieved through one or more known techniques such as an output file, printer, facsimile, e-mail, web-posting, or the like. Storage may be achieved internally and/or externally and may include, for example, a hard drive, CD drive, DVD drive, tape drive, floppy drive, network drive, flash, or the like. The processor may use any type of monitor or screen known in the art for displaying information. For example, a cathode ray tube (CRT) or liquid crystal display (LCD) can be used. One or more display panels may also constitute a display. In other embodiments, a traditional display may not be required, and a processor may operate through appropriate voice and/or key commands.

The above system shows a non-limiting embodiment. One of ordinary skill in the art can recognize each component may be optional. Alternatively, more than one of each component may be provided.

Microfluidic Cell

Figure 2:
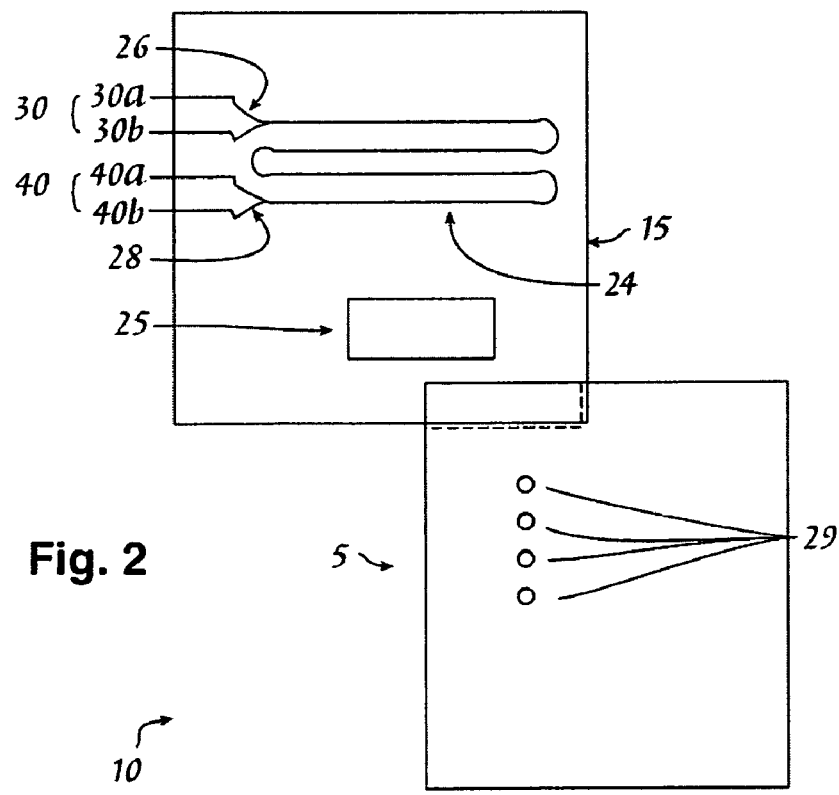
FIG. 2 shows a microfluidic cell in accordance with embodiments of this disclosure.

FIG. 2 shows a close-up view of microfluidic cell 10 comprising any suitable material, such as, but not limited to glass, silicon, plastic, quartz, metal, resin, and/or other chemical resistant materials or other transparent material known in the art. Microfluidic cell 10 may include a substrate comprising a plurality of microchannels (e.g., channel 24 of FIG. 2) that may be configured for parallel multilayer flow such as the system described in U.S. Patent Publication No. 2004/0219078, incorporated herein by reference in its entirety. In some aspects, microfluidic cell 10 may include a plurality of microchannels (e.g., channel 24) that may be arranged on various positions of microfluidic cell (e.g., two or more channels placed adjacent to one another). Each of the different microchannels may be in communication with another microchannel via a guide microchannel that identifies a specific fluid.

Microfluidic cell 10 may include a plurality of substrates that may be laminated together such that the microchannels are arranged on surfaces of different substrates, and may be vertically configured to allow different microchannels to communicate with another microchannel through a vertically penetrating guide hole for transporting a fluid.

In other aspects, microfluidic cell 10 may include a plurality of substrates that are laminated, wherein an inlet (e.g., inlet 30) for supplying a fluid to the multilayer flow microchannel and an outlet (e.g., outlet 40) for discharging a fluid from microchannel 10 are each arranged on the surface of the same or different substrate. Each of the above microchannel configurations may provide for a multilayer flow operation, where a multilayer flow includes gas/liquid interface or a liquid/liquid interface (e.g., aqueous/organic phase) that may be formed within the microchannel. In one aspect, the microchannel configurations may be adapted to perform a single type of unit operations including, without limitation, mixing/reacting, extraction, separation, identification, quantification, and/or authentication.

The microchannels of microfluidic cell 10 may be coupled to a guide structure (not shown). In one aspect, the guide structure may be coupled to a bottom-side of the microchannels. Alternatively, the guide structure may be coupled to the microchannels in a position corresponding to parallel interfaces of the fluids forming a multilayer flow through the microchannels. In this configuration, the guide structure may extend toward the flow direction and provides stabilization at liquid/liquid interface or a gas/liquid interface.

In some aspects, the microchannel may have a width of about 500 micrometers or less and a depth of about 300 micrometers or less. In one embodiment, the microchannel may include dimensions in the range of about 50 to 100 micrometers in width and about 25 to 50 micrometers in depth. These dimensions offer the advantages of reduced fluid volume over the microfluidic cell. Very small quantities of fluids are needed to fill the microchannels and thus, a material may be readily identifiable in a more efficient manner, while minimizing waste products and contamination.

The microchannel may be determined based on the material to be authenticated and other design configurations. The microchannels of microfluidic cell 10 may be fabricated using, for example, silicon processing techniques such as, but not limited to chemical processing steps known in the art. Such steps may include, without limitation, a deposition process (e.g., physical vapor deposition, chemical vapor deposition, electrochemical deposition, molecular beam epitaxy, or atomic layer deposition), a stripping process (e.g., wet etching, dry etching, ion milling, plasma etching, reactive ion etching or chemical-mechanical planarization), a patterning process (e.g., lithography), and/or a modification of electrical or mechanical properties (e.g., implantation or anneal).

It is known in the art that certain fabrication processes are preferred over others.

For example, a dry etch process may be preferred due to its ability to control the process (e.g., selectivity of materials), and thus, may provide certain microchannel profiles that are unique over other methods. For example, reactive-ion etching (RIE) is a method of dry etching that uses a combination of mechanical and physical etching mechanisms. An RTR process may provide unique profiles due to its judicious selection and optimization of reactant gases, pressure, temperature, and power sources. RTJB can thus attain a high degree of anisotropy (one-direction) as well as selectivity, preferably in high aspect-ratio etching.

Referring again to FIG. 2 in some embodiments, microfluidic cell 10 may include two portions, an upper portion 5 and lower portion 15. In some aspects, upper portion 5 may include a different material than lower portion 15. Alternatively, the upper portion 5 and the lower portion 15 may include a similar material. Upper portion 5 may fit onto lower portion 15 and, in some embodiments, the two portions may be sealed using a chemically resistant seal known in the art.

In one example, upper and lower portions 5 and 15 may include two optically polished glass plates. Lower portion 15 may include an etched channel etched with an approximate length of about 8.5 cm, a width of about 60 micrometers, and a depth of about 25 micrometers, although other dimensions may be suitable. Each end of the etched channel may be bifurcated into two channels in a Y shape and each of these bifurcations may be coupled to a capillary. Each capillary may be coupled to a bifurcated channel through the upper portion 5, which may be used as a cover. In some embodiments, two capillary inlets may enter a microchannel through upper portion 5 and may exit through the lower portion 15.

In some aspects, upper portion 5 and lower portion 15 may be an integral unit. In one embodiment, upper portion 5 and lower portion 15 may be sealed together using, for example, chemically resistant ceramic glue, fusion bonded or any other adhesive known in the art.

In some embodiments, each of the capillaries may be about 10 cm long with an internal diameter of about 100 micrometers. These capillaries can be interfaced to other capillaries or to ends of pumps using additional tubing, such as polytetrafluoroethylene (PTFE) tubing of the correct internal diameter. In one example, where multiple capillaries are available, one capillary outlet may be blocked, so that only one capillary outlet may be operating. This single operable capillary outlet may be coupled to a detection assembly, using a PTFE sleeve.

The configurations of microfluidic cell 10 described above are intended to be non-limiting examples. One of ordinary skill in the art can understand that the microfluidic cell may be modified. For example, the microfluidic cell may include one inlet for receiving a material comprising at least one latent marker. The inlet may also receive an agent that may transform the latent marker to an active marker. Alternatively, a separate inlet may be provided to receive the agent.

As the material and agent are traversing through the microfluidic cell, a detector comprising a light source coupled to the microfluidic cell may irradiate the fluid flow and excite the activated markers. The emission from the activated markers may be collected using, for example, a sensor coupled to the detector. The collection of the signals may continue until the liquids (the agent and the material including the marker) exit the microfluidic cell via an outlet.

Identification and Quantification of a Marker to Authenticate a Material

In one embodiment, for identification, quantification, and authentication of a solid material comprising latent markers, one or more portions of the solid material may be removed and suspended in a liquid, where the one or more portions may dissolve in the liquid. In one aspect, the solid material may include markers (e.g., glue ink, security ink, and other suitable markers) that may be evenly distributed throughout the material. In particular, the one or more latent markers may dissolve in the liquid and may be detectable using techniques of the present disclosure.

For identification, quantification, and authentication of a material in liquid form, the material including latent markers may be introduced into the one or more channels via inlet 30*a*. The material may include, without limitation, a fuel, a lubricant, spirits, liquid pharmaceuticals, or any other fluids that require marking in order to preserve the integrity and authenticity of the fluid.

An agent capable of transforming the latent form of the marker into an active form may be provided to the channels via inlet 30*b*. In some embodiments, the agent may be introduced to the microfluidic cell at about substantially the same time as the liquid material. The agent may be any suitable agent that promotes transformation of the covert marker. For example, the agent may include, without limitation, an acidic solution or a basic solution. Alternatively, the agent may be an element (e.g., oxygen, metal compound, and the like) that may bond with or alter the physical and/or optical characteristics of the markers such that it may be detectable. The agent may include an anti-Stokes luminescent compound, as described in U.S. Patent Publication No. 20050260764, entitled "Method and Apparatus for Monitoring Liquid for the Presence of An Additive," by Grisby et al., which is incorporated herein in its entirety. Other suitable agents capable of changing a physical or chemical property of a latent marker to an active marker may also be used.

In some embodiments, the agent may be suspended in a liquid. The liquid may be a solvent that prevents further modification of the active form of a marker. Examples of the solvent (e.g., agent) may include, without limitation, octanol, butanol, ethanol, octanes, hexanes, alcohol strings of suitable lengths, and other suitable aqueous solutions. Thus, the active form of a marker may be in a detectable form that can be readily quantifiable. For example, upon leaving microfluidic cell 10, the active form of the marker may be an analyte that may be detected by a detector such as detection component 50 (shown in FIG. 1). In some embodiments, the markers may be present in the one or more outlets 40 (e.g., 40*a* and/or 40*b*) as shown in FIG. 2. In other embodiments, when a single detector is in use, only one outlet may be necessary. As such, outlet 40*a* may be active while outlet 40*b* may be blocked or vice versa. Alternatively, the markers may be present within a channel (e.g., channel 24) of the microfluidic cell and may be detected using a detector coupled to the microfluidic cell.

In some embodiments, a surfactant may be added prior to, at the same time as, or after the introduction of the agent and liquid material via an inlet coupled to a channel of the microfluidic cell. The surfactant may modify the surface of the channels (e.g., reduce surface tension) and thus, may influence the flow of fluids. In one aspect, the surfactant may include, without limitation, butanol, or other hexanol surfactants.

Figure 3A:
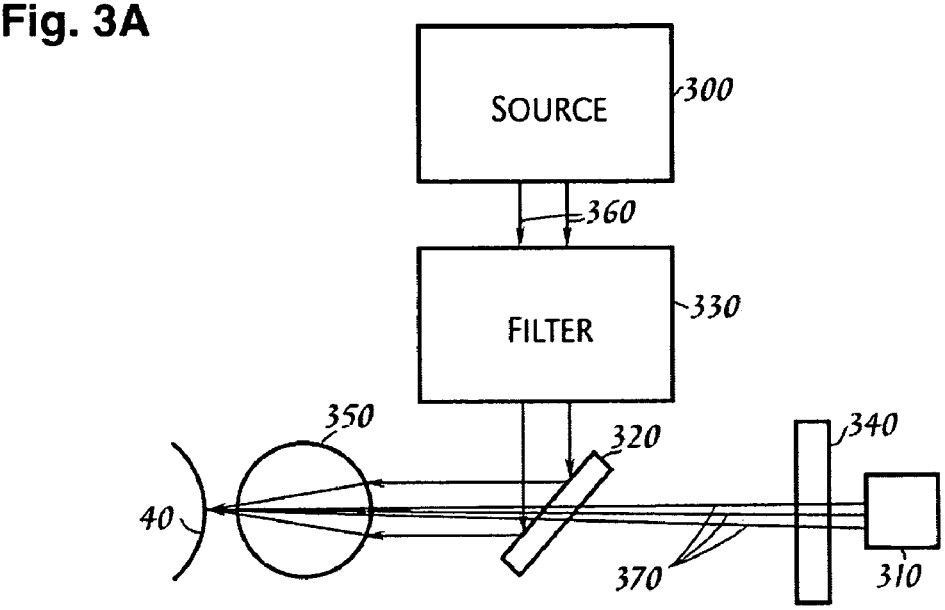
FIGS. 3A, 3B, and 3C show a detection component in accordance with embodiments of this disclosure.

Liquids (e.g., fluid to be authenticated, agents, etc.) entering the microfluidic cell 10 may flow in a single direction, entering from the at least one inlet 30 (e.g., 30*a* and 30*b*) and exiting the one or more outlets 40 (e.g., 40*a* and 40*b*). To promote optimal flow of liquid through the device of the present invention, inlets 30*a* and 30*b* and the one or more outlets 40 (e.g., 40*a* and/or 40*b*) are of similar diameter to each other and to the one or more channels (e.g., channel 24). Alternative fittings (e.g., outlet and inlet ports coupled to the capillaries) may be used as appropriate. In some embodiments, inlets 30*a* and 30*b* fit into channel 24, where inlets 30*a* and 30*b* form an integral unit. Alternatively, inlets 30*a* and 30*b* may be two separate and distinct inlets, each coupling to inlet fork 26. Similarly, outlets 40*a* and 40*b* may be an integral unit or may be two distinct components coupled to channel 24 through outlet fork 28. Inlet fork 26 and outlet fork 28 may exist as separate components or may be continuous with the channel. When an inlet contacts a channel (with or without a fork or other such fitting), the inlet may enter through upper portion 5 via top openings 29 or side openings (not shown) or may fit into lower portion 15 via side or bottom openings (not shown) or may enter between upper portion 5 and lower portion 15 (not shown). Referring to FIG. 3A, a schematic of detection component 50 is shown. Detection component 50 may include electromagnetic radiation source 300, sensor 310, and beam splitter 320. In some embodiments, first filter 330 and second filter 340 may be included, although one of ordinary skill in the art may recognize that the filters may be optional components. Example of source 300 may include a light emitting diode, a laser, a bulb, or the like capable of providing an ultraviolet wavelength, a visible wavelength, an infrared wavelength, or a combination thereof. In one embodiment, beam splitter 320 may include, without limitation, a dichroic beam splitter. An example of sensor 310 may be a photodiode, although other suitable sensors may be used. In one embodiment, sensor 310 may include integrated amplifier and additional data collection, data analyses, and data storage components as are known to one of ordinary skill in the art.

In one aspect, detection component 50 may be placed in a housing for ease in positioning of the component. Machined plastic or other suitable materials may serve as the housing.

One or more outlets may be coupled detection component 50. Outlets may include one or more outlets 40 which may be positioned proximate to optical lens 350. Detecting outlet 40 may be optionally coated for protection. In some embodiments, the coating may be removed in areas where heat is present.

In one embodiment, optical lens 350 may be positioned to receive one or more excitation rays 360 from source 300, as shown in FIG. 3A. In some embodiments, excitation rays 360 may be filtered or have their spectral range adjusted by first filter 330 prior to being received by lens 350.

Beam splitter 320 may direct excitation rays 360 (filtered or unfiltered) towards optical lens 350. Lens 350 may receive the excitation rays 360 and may focus rays 360 onto the one or more outlets 40, where outlets 40 may include markers that may have optical characteristics that may be observable.

Emission rays 370 from the markers at outlets 40 may be filtered via second filter 340, and may subsequently be collected by sensor 310. Filter 340 may remove certain wavelengths introduced as the emission rays 370 pass by the splitter and/or other background wavelengths introduced during the transmission between the marker(s) and sensor 310.

Other adjustments may be made to emission rays 370 prior to being collected by sensor 310 including, without limitations, focusing a focusing lens, polarization using a polarizer, and/or other suitable processing techniques known in the art.

Figure 3B:
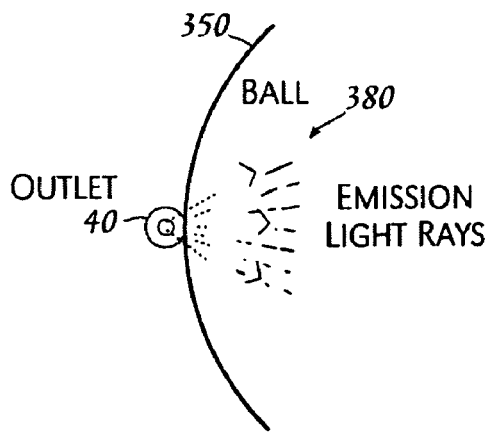
Figure 3C:
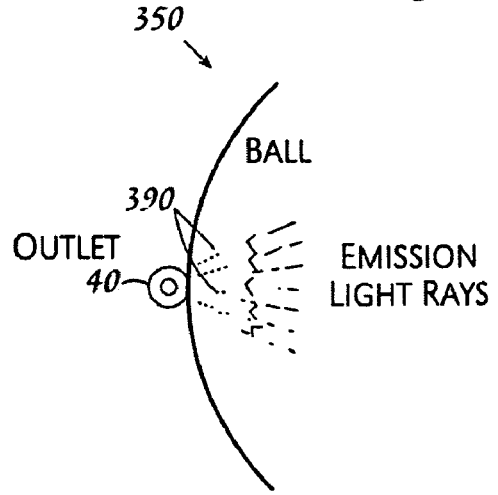

Referring to FIGS. 3B and 3C, side views illustrating possible configurations for the detection of one or more markers carried by the one or more outlets 40 are shown. FIG. 3B illustrates the possible positions of emission rays 380 after being excited with source 300, contacting beam splitter 320, and passing through optical lens 350. FIG. 3C illustrates the possible positions of excitation rays 390 after emission rays 380 contact outlets 40 via optical lens 350.

Optionally, the markers and agent may be removed from outlet 40 and provided to detection component 50, remotely set apart from the microfluidic cell, using, for example, the liquid transfer systems, other capillaries, inlets, outlets, and a storage means for housing the markers and agent during the detection process. FIGS. 3A, 3B, and 3C can be modified to include a storage means coupled to spherical lens 350 instead of outlets 40.

Figure 4:
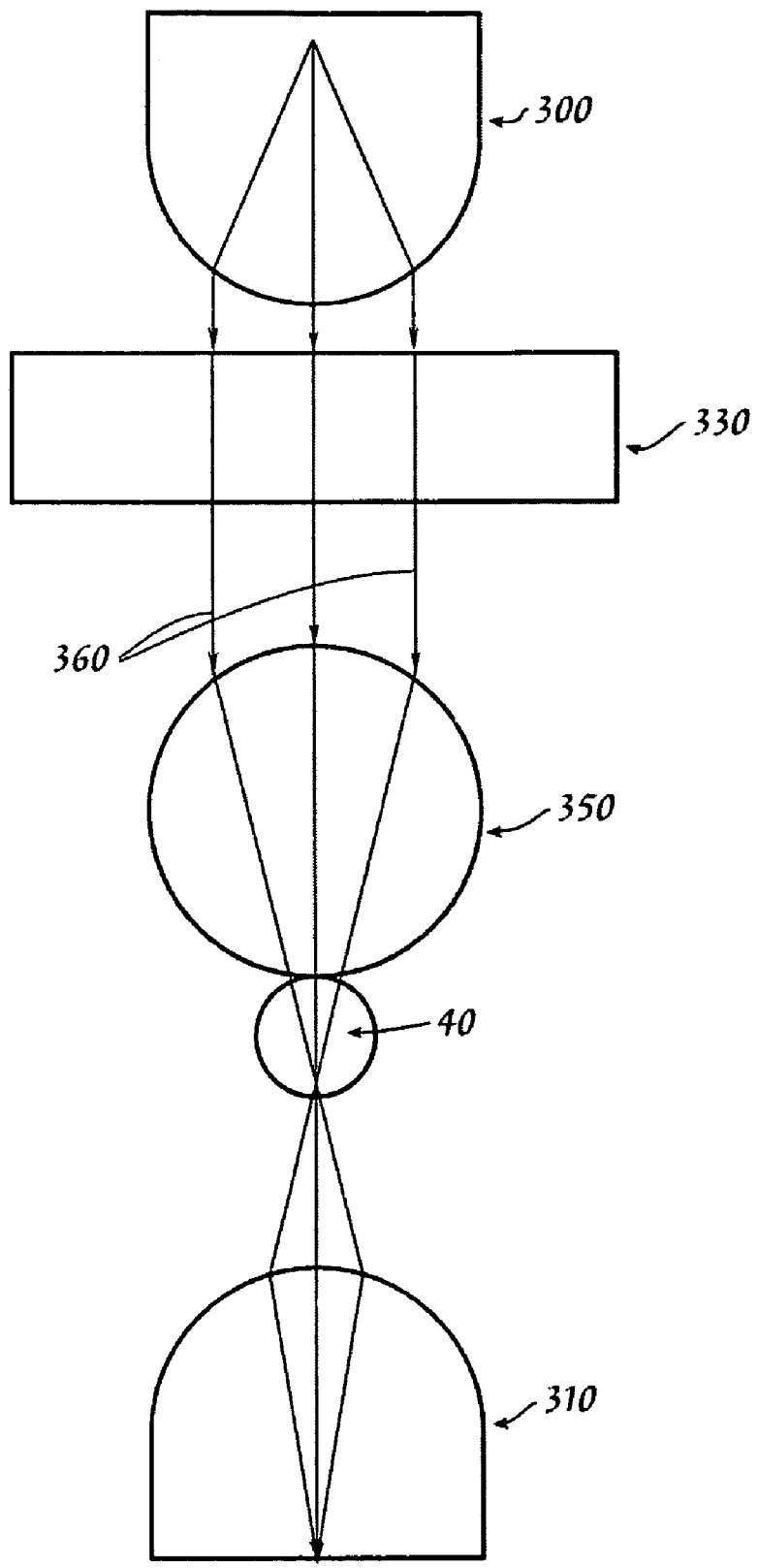
FIG. 4 shows a detection component in accordance with embodiments of this disclosure.

In alternative embodiments, a detection component may be configured to detect absorption, as shown in FIG. 4. Excitation rays 360 from source 300 may be optionally filtered with filter 330 and subsequently directed towards optical lens 350, which may be aligned with source 300 to receive excitation rays 360. Optical lens 350 may focus rays 360 onto the one or more outlets 40, which may include one or markers (e.g., latent and/or activated). The illumination from excitation rays 360 may be absorbed by the markers and may cause the markers to emit a detectable signal, collected by detector 310. Additional objects, advantages and novel features of the invention as set forth in the description, will be apparent to one skilled in the art after reading the foregoing detailed description or may be learned by practice of the invention. The objects and advantages of the invention may be realized and attained by means of the instruments and combinations particularly pointed out here.

EXAMPLES

The following examples are included to demonstrate specific embodiments of this disclosure. It should be appreciated by those of ordinary skill in the art that the techniques disclosed in the examples that follow represent techniques discovered by the inventors to function well in the practice of the invention, and thus can be considered to constitute specific modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

The Effect of Flow Rate

The rate of transformation (from latent to active form) often depends on the flow rate through the microfluidic cell. For example, lower flow rates may allow for improved and increased diffusion of the markers from the liquid (e.g., a fuel) to the transforming agent, and thus, higher fluorescent signals may typically be detected. In addition, the extent of transformation and signal level often depends on channel volume and quantity of the transformable marker. In some embodiments, capillary and channel diameters may also affect reaction time.

A fluorescent signal was detected using a detector/detection assembly similar to that described in FIG. 3A. Components of the system were housed in a machined plastic unit. A BrightLite filter set (Semrock, New York) optimized for measuring green fluorescent protein (GFP) was used. A light emitting diode (Roithner Lasertechnik, Austria) with a maximum output of about 470 nm was used as the source. The sensor had an integrated amplifier. The optical lens was a 5.0 millimeter diameter spherical lens from Edmond Optics (United Kingdom). Detection was measured from a single capillary outlet coupled to the above-described detection assembly through a detecting capillary. In some embodiments, the detection technique may include, without limitation, luminescence, fluorescence, absorption, or anti-stokes. The capillary outlet was coupled to the detecting capillary via a PTFE sleeve. The detecting capillary (Polymicro Technologies, Arizona) had an internal diameter of about 150 micrometers, an external diameter of about 375 micrometers, and was coated with polyimide. The coating was removed from the detecting capillary in certain areas where radiation may be present. The detecting capillary was positioned to generally touch the spherical lens. Data collected from each run was averaged over a 5.0 second period with a time constant of 3.0 milliseconds and a sampling rate of 512 readings per second.

Figure 5:
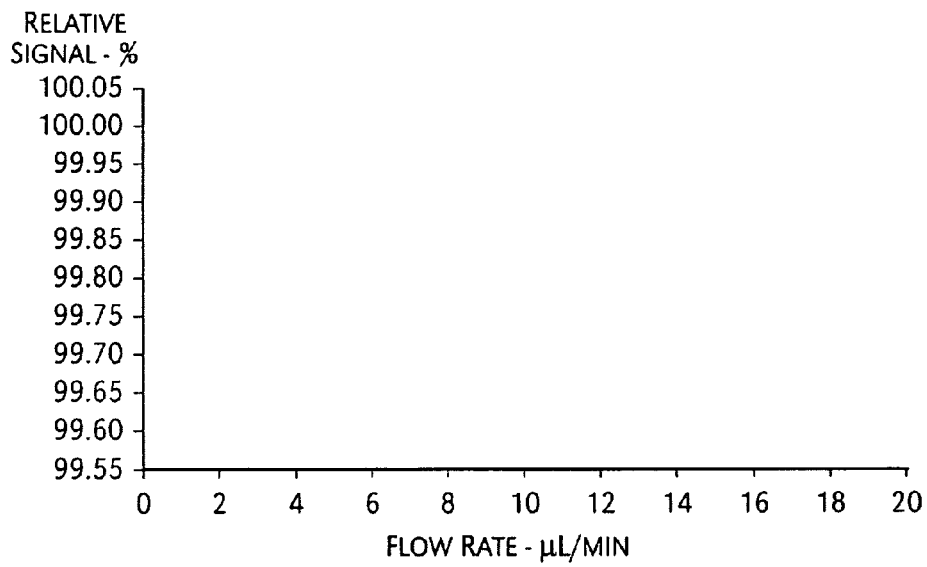
FIG. 5 is a graph illustrating flow rate effects in accordance with embodiments of this disclosure.

In this example, the concentration was $10 \times 10^{-9}$ grams of marker per milliliter of ethanol. As shown in FIG. 5, changes in flow rate did not significantly affect the rate of transformation (e.g., hydrolysis), as reflected by the relative signal detected by the detection component. Even a large reduction in the flow rate from 17.65 to 2.5 microliters per minute affected the reaction yield by only about 0.5%.

Figure 6:
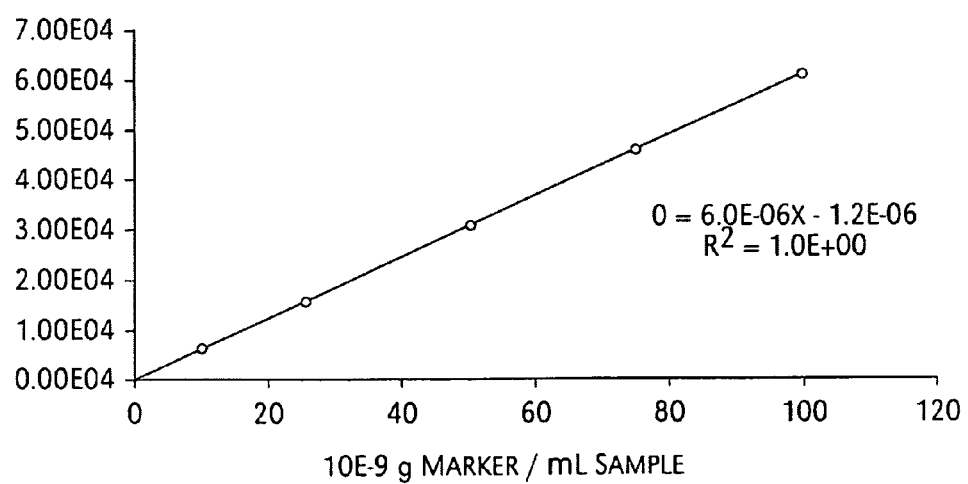
FIG. 6 is a graph illustrating linearity in accordance with embodiments of this disclosure.

Subsequent analyses showing the quantitative nature of the present invention were performed using flow rates of 10 microliters per minute from each syringe. FIG. 6 shows the relationship between the detection signal and the concentration of the marked sample, when flow rate was constant at 10 microliters per minute. Here, the detection signal correlated with marker concentration ($R^2=1.0$). This shows that the present disclosure is suitable for detecting a covert marker at very low concentrations, even those on a nanoscale.

Accordingly, the presence of an additive or marker in a material (e.g., ethanol) may be identified and quantified. The quantification of the markers yielded extremely low levels of adulteration, levels which are suitable for forensic testing or other such analysis requiring evidence of misuse or authentication. In addition, analyses with the present disclosure are reproducible, have very narrow error margins (if any), require little sampling material, produce very little waste, and present results in a matter of minutes or less that are quantifiable. The present invention is also robust and not delicate and therefore, suitable for use in the field or for in situ analysis.

Example 2

Authenticating Potable Ethanol

Potable ethanol is often adulterated illegally with lower grade product, and thus poses a need for a reliable, robust, and convenient authentication method. In this example, non-potable ethanol was marked with a covert marker and used to enable identification and authentication of potable ethanol adulterated with the non-potable form.

The marker used to identify non-potable ethanol was fluorescein diacetate, a marker that has no significant fluorescence when dissolved in ethanol. While fluorescein diacetate was used, any suitable marker with similar properties may be used. This includes markers that reside in an inactive form and may be transformed to an active form that is identifiable and quantifiable by a detector. Fluorescein diacetate may be transformed (via hydrolysis) in alkaline solutions to produce fluorescein to an active form with light-emitting properties that are detectable by an appropriate light detector.

In one example of the present disclosure, fluorescein diacetate was dissolved in non-potable ethanol at a concentration of 10 micrograms per milliliter. This concentrated solution was then used to covertly mark non-potable ethanol at final concentrations ranging from about 10 to 100 nanograms of marker per milliliter of non-potable ethanol. The final concentrations of fluorescein diacetate used in the example were: $10 \times 10^{-9}$ grams/mL of ethanol, $25 \times 10^{-9}$ grams/mL of ethanol, $50 \times 10^{-9}$ grams/mL of ethanol, $75 \times 10^{-9}$ grams/mL of ethanol, and $100 \times 10^{-9}$ grams/mL of ethanol.

The alkaline solution was 2.0 mole per liter of sodium hydroxide prepared by dissolving 0.8 grams of sodium hydroxide in a mixture of 5.0 milliliters of water and 5.0 milliliters of methanol. The 10 milliliters of alkaline solution was sufficient to perform hundreds of analysis runs with the present disclosure. Simultaneous introduction of the marked ethanol and the alkaline solution were performed using a dual syringe driver. The dual syringe driver was capable of delivering liquid from each of the two syringes at flow rates of up to 17.65 microliters per minute. The marked ethanol was pumped into the microfluidic cell via one capillary inlet, and the alkaline solution was simultaneously pumped into the microfluidic cell via a separate capillary inlet, producing a laminar, parallel flow. Transformation of fluorescein diacetate occurred in the microfluidic cell in the presence of the alkaline solution after which the solution exited the cell and was identified and quantified by a detector. Typically, transformation and detection was complete after a few minutes.

For analysis, the lowest concentration of marked ethanol was used first; each subsequent concentration used was of a greater concentration. The extent of transformation (in this case, hydrolysis) was tested by varying the flow rate. Flow rates of 2.5, 5, 7.5, 10, 12.5, 15, and 17.65 microliters per minute were used. With each run, liquid from each of the capillary inlets filled the channel of the glass support within seconds. It is noted that transformation can be performed using other techniques, including, without limitation, oxidation, reduction, structural modification (e.g., dissolving the marker), ionization, electrolysis, complexation, or a combination thereof.

Example 3

Plug Flow

In another aspect, system 65 of FIG. 1 may be modified to include a reservoir/mixer for providing a plug flow. In one aspect, a material comprising latent markers and a first agent (e.g., aqueous ethanol) that may transform the latent markers may be introduced to a microfluidic cell using techniques described above (e.g., using a pump system and the like). The introduction of the material simultaneously with the agent provides a laminar flow.

Figure 7:
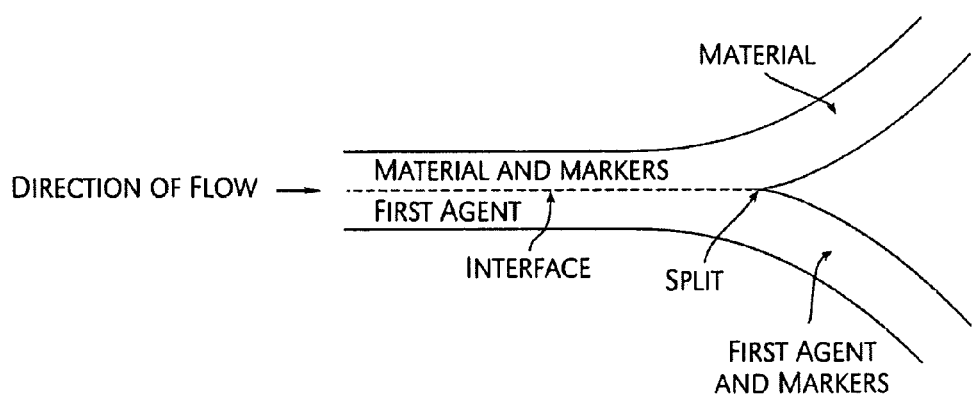
FIG. 7 shows a plug flow in accordance with embodiments of this disclosure.

In one aspect, the material may subsequently be split from the latent markers and removed via an outlet (e.g., outlet 40 of FIG. 2), leaving only the latent markers. For example, referring to FIG. 7, as the material 700 and markers 702 flow through the microchannel 24, the markers may penetrate through the interface 704 into the first agent 706, and thus at the split 708, the material may be subsequently removed, leaving the marker 702 and first agent 706. In one aspect, a driving equilibrium (e.g., pH levels) may be adjusted causing the markers to diffuse from the material to the first agent.

Figure 8:
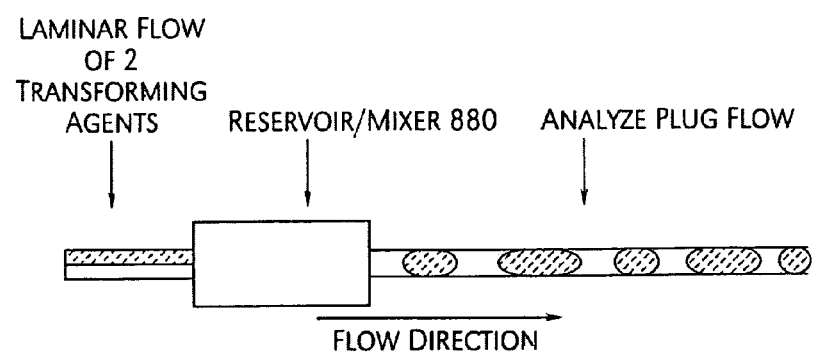
FIG. 8 shows a laminar flow in accordance with embodiments of this disclosure.
Figure 9:
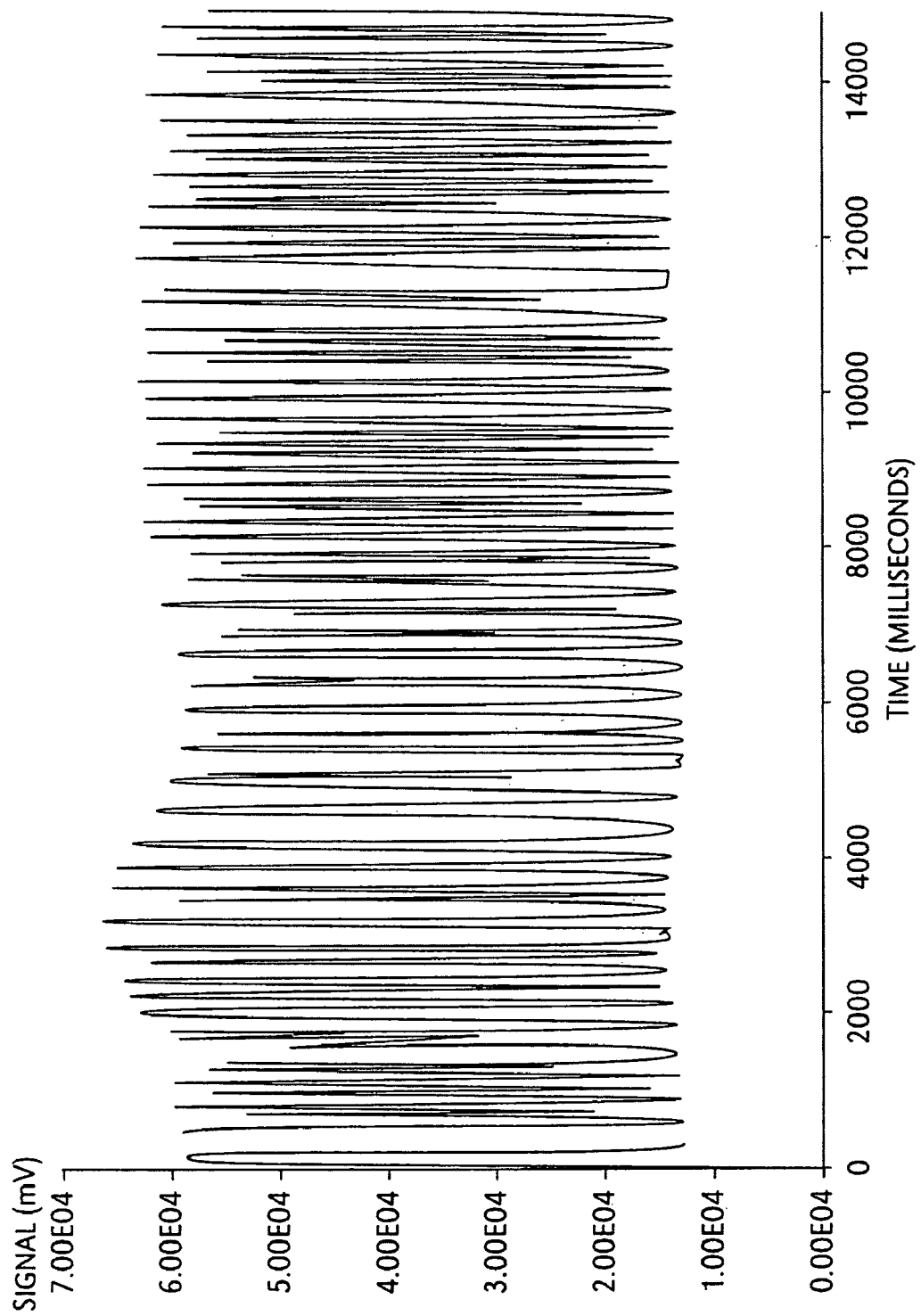
FIG. 9 is a graph of a signal detected from activated markers in accordance with embodiments of this disclosure.

Next, a second agent (e.g., octanol) may be added to the latent markers to produce another laminar flow between the first and second agent, as shown in FIG. 8. This laminar flow may be passed through reservoir/mixer 880 which mixes the two fluid streams 800, 802 and transforms the latent markers. The result is a plug flow 804 that includes activated markers that can be identified and quantified. Subsequent authentication of the material may be also performed, using techniques of the present disclosure. Referring to FIG. 9, a graph illustrating the signal detected using the above techniques corresponding to the concentration of the markers is shown.

The above embodiment provides a simple technique that eliminates a need of a second separation step of the two liquid phases.

Example 4

Plug Flow Extraction

One aspect of the invention features use of plug flows to extract a marker from a host fluid into one or more transfer agents. Slug flows may also be used in aspects of the present invention.

Figure 10:
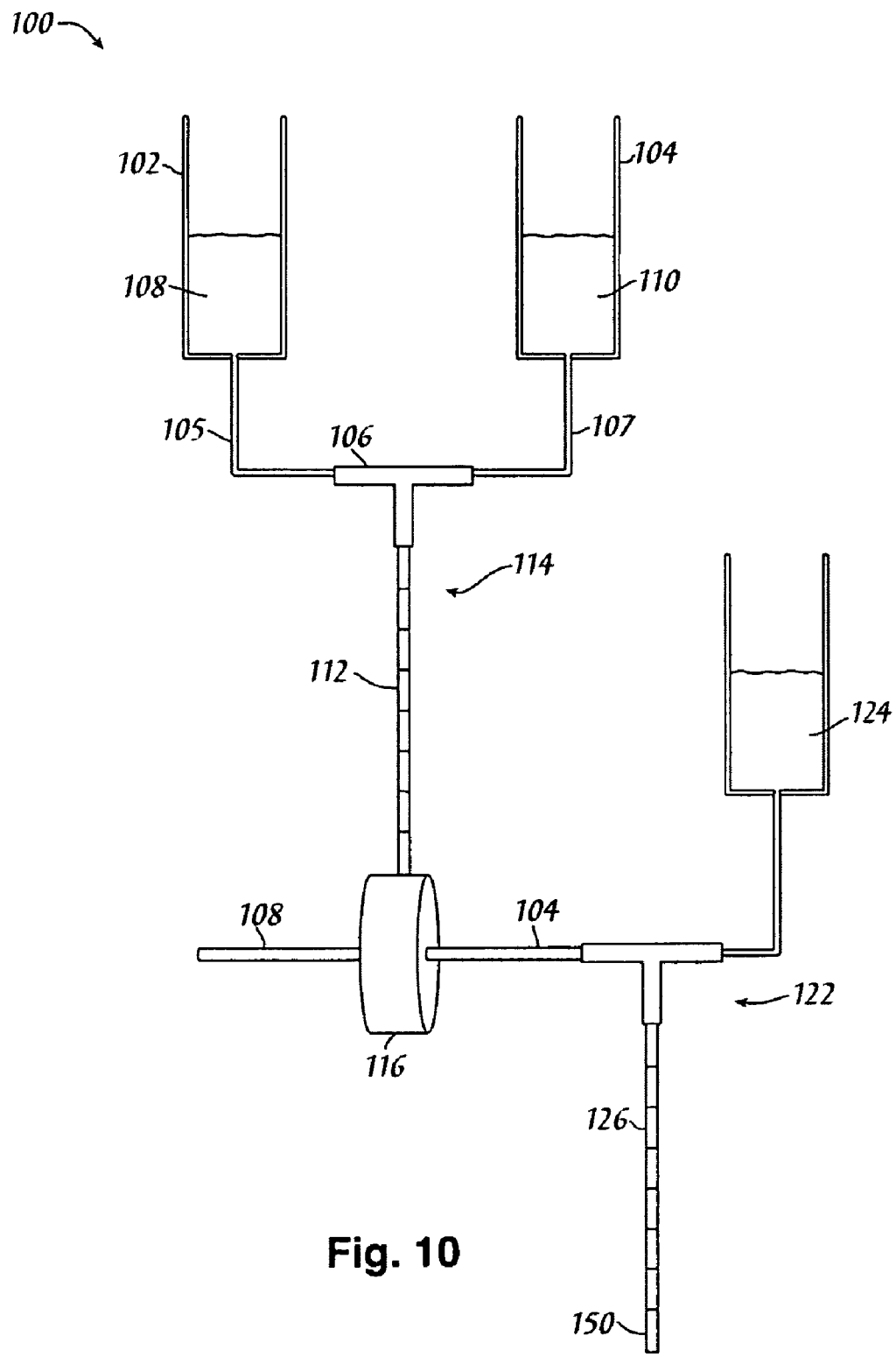
FIG. 10 is a schematic view of a plug flow marker extraction system.

FIG. 10 illustrates a schematic of a plug flow extraction system 100 including first and second fluid sources 102 and 104 coupled to respective inlets 105 and 107 of a mixer 106, e.g., microfluidic block, T-junction or Y-junction. Fluid source 102 provides a first fluid 108, e.g., a fuel, with a trace of one or more covert markers 103, and fluid source 104 provides a first marker transfer agent 110, e.g., an aqueous solution. Mixer 106 is configured to provide a mixed plug flow 112 (sometimes referred to as slug flow or segmented flow) of fluid 108 and agent 110 in a plug flow conduit 114.

In general, plug flows are produced by flowing two immiscible liquids (fluid 106 and agent 108) at equal flow rates through a mixer 106 such as a T-junction or Y-junction, for example. The different surface energies of the two immiscible liquids produce alternate fluid plugs in plug flow 112. As plug flow 112 of fluid 108 and agent 110 travels through plug flow conduit 114, counter currents and frictional forces cause interaction of the liquids and partial transfer of markers 103 from fluid 108 to transfer agent 110. In general, fluid interaction over increasing lengths of flow conduit 114 produce increased transfer or extraction of markers 103 from fluid 108 into the initially unmarked transfer agent 110. Extraction efficiency is dependent on, among other variables, flow velocity, plug length, plug conduit diameter and length and liquid viscosity. Conduit 114 can be any tube, channel, or the like suitable to convey a plug flow.

A splitter 116 is then used to separate fluid 108 and transfer agent 110, which now contains traces of markers 103. In some embodiments, splitter 116 may quickly separate the two immiscible liquids without high pressures or temperature. Splitter 116 includes filters 118 and 120 with different surface energies. For example, filter 118 may be a lipophilic membrane filter and filter 120 a hydrophilic membrane filter. In one example, the membranes can be wetted with hydrophobic or lipophobic materials. As plug flow 112 passes through phase splitter 116, filters 118 and 120 each pass one fluid while blocking the other producing two distinct and separate streams of fluid 108 and agent 110, which contains marker 103. Fluid 108 may then be disposed of or recycled. Filters 118 and 120 can be any type or configuration of filters suitable to separate a plug flow into two distinct phases. For example, a single filter can be used in some cases to pass one phase of the plug flow leaving the other phase of the plug flow.

A second plug flow mixer 122 may be implemented to produce a second plug flow 126 with a second transfer agent 124, e.g., an organic solvent. Second plug flow 126 causes a second transfer or extraction of marker 103 into the second transfer agent 124 so that marker 103 is more amenable to detection by detector 150. For example, some markers may require double extraction, e.g., from a petroleum-based fuel to an aqueous solution and then to an organic solvent, to render the marker optimally detectable or identifiable. Second plug flow mixer 122, in some cases, may be connected directly to an output of splitter 116. Plug flow mixers 106 and 122 can be configured as any junction of multiple streams of material suitable to produce a plug flow of the materials.

In other embodiments, transfer agent 110 with marker 103 may be received from splitter 116 by detector 150 without a second extraction step. For example, some markers may be readily identified by detector 150 with a single extraction process. Any number of additional extraction and splitting steps may be used in other embodiments of the invention. For example, two plug flow extraction steps may be used to isolate a marker while a third plug flow step is used to activate a marker. Similarly, various detectors may be positioned between different extraction stages.

Figure 11:
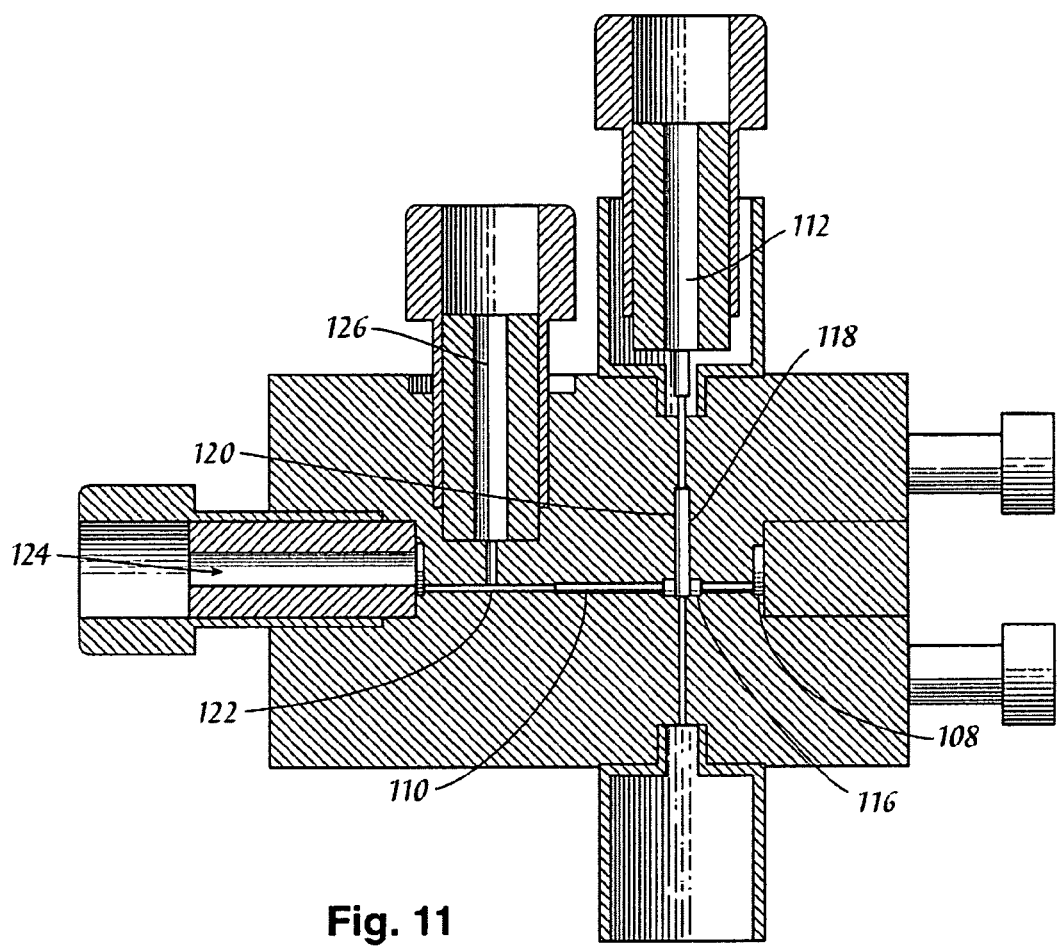
FIG. 11 is a cross-sectional view of a phase splitter in combination with a secondary plug flow.
Figure 12:
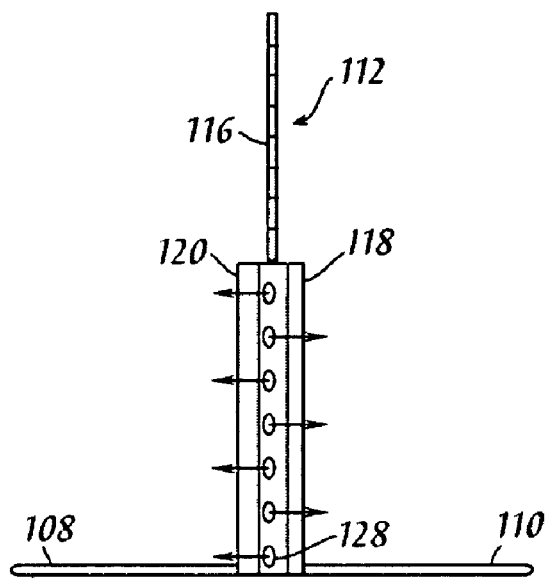
FIG. 12 is a cross-sectional schematic view of a phase splitter.

FIG. 12 shows a schematic cross-sectional view of the phase splitter 116 design of FIG. 11. Splitter 116 may be configured to efficiently separate the fluids with minimal cross-contamination. In one embodiment, plug flow 112 enters phase splitter 116 through a tube with 0.5 mm internal diameter, into a central filter chamber 128. Chamber 128 is 6 mm in diameter with a separation of 600 microns between filter membranes 118 and 120. It has been determined to be advantageous in some embodiments for the separation of filters 118 and 120 to be approximately equal to the diameter of the plugs entering chamber 128. This configuration allows the different surface energies of filters 118 and 120 to attract or repel the respective fluid to provide efficient, continuous separation of the liquids. Excess separation between filters 118 and 120 is believed to cause dead volume and possibly increase cross-contamination resulting in reduction of splitter efficiency. Extraction of the marker through a plug flow and separation of the flows in a splitter can be performed in some cases in a matter of minutes.

Figure 13:
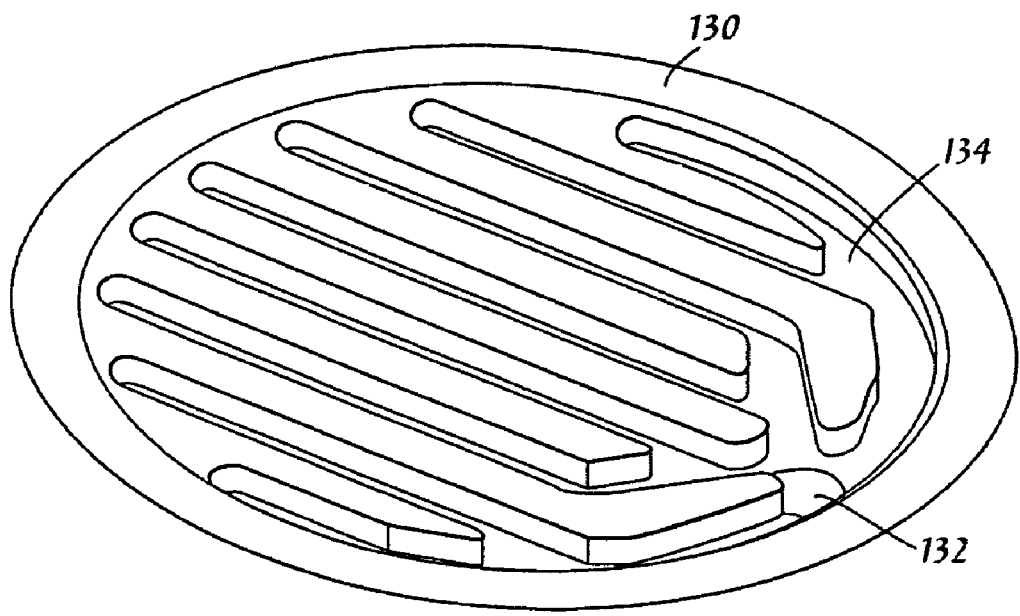
FIG. 13 is a perspective view of a filter support.

FIG. 13 illustrates one embodiment of a filter support 130 disposed at a lower portion of filter chamber 128. Filter support 130 is sloped towards an outlet 132 and defines a network of dendritic grooves 134 to guide a fluid to outlet 134. In some cases, outlet 132 is diametrically opposed to a chamber inlet (not shown). A corresponding upper filter support (not shown) can be of similar construction and can have an outlet positioned on an upper portion, side portion, diametrically opposed to the inlet, or the like. Different filter support configurations can be used with different filter arrangements and may include or be used with, for example, discrete channels, common chambers, inclined surfaces, multiple inlets or outlets, sedimentation paths, multi-stage filters, valves, or any number of other filtration features.

Figure 14:
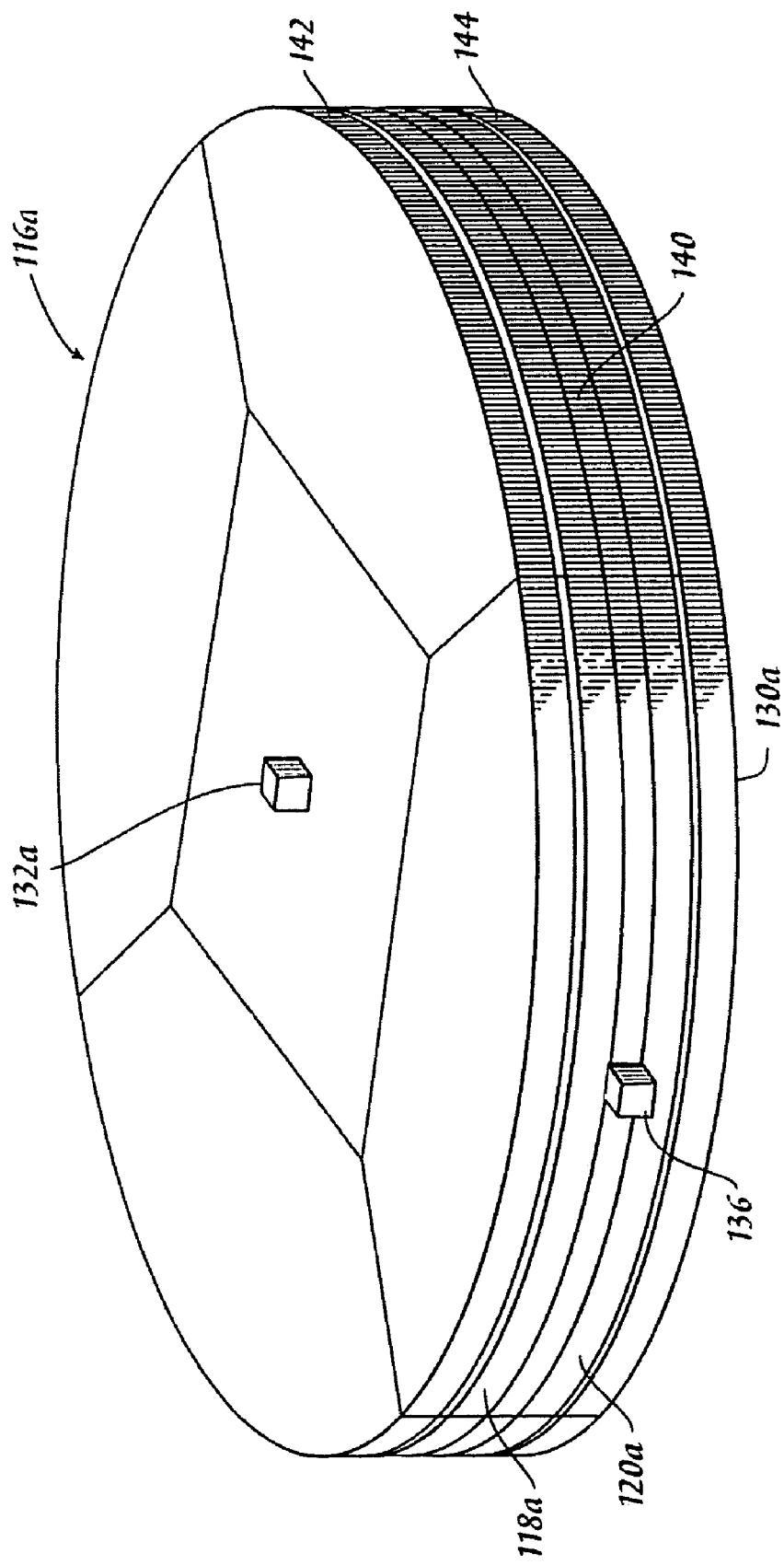
FIG. 14 is a cross-sectional view of a splitter.

FIG. 14 illustrates another splitter 116a including a lateral inlet 136 supplying an inlet chamber 140 defined by filters 118a and 120a, a centralized upper outlet 132a for allowing flow of one separated fluid from a first outlet chamber 142 and a second lower outlet (not shown) for allowing flow of a second separated fluid from a second outlet chamber 144. Outlet chambers 142 and 144 are defined by filters 118a or 120a on one side and a filter support 130a on the other.

Separation time, or "flushing" time, through splitter 116 can be influenced by a number of variables affecting the fluid dynamics in the splitter, (for example, the size and shape of each of chambers 140, 142 and 144, the diameter and position of inlet 136 and outlet 132a). For example, an inlet chamber height of 400 µm and an outlet chamber between 100-300 µm high with a chamber diameter of between 5-10 mm provides suitable separation time for a fuel-water plug flow.

Figure 15:
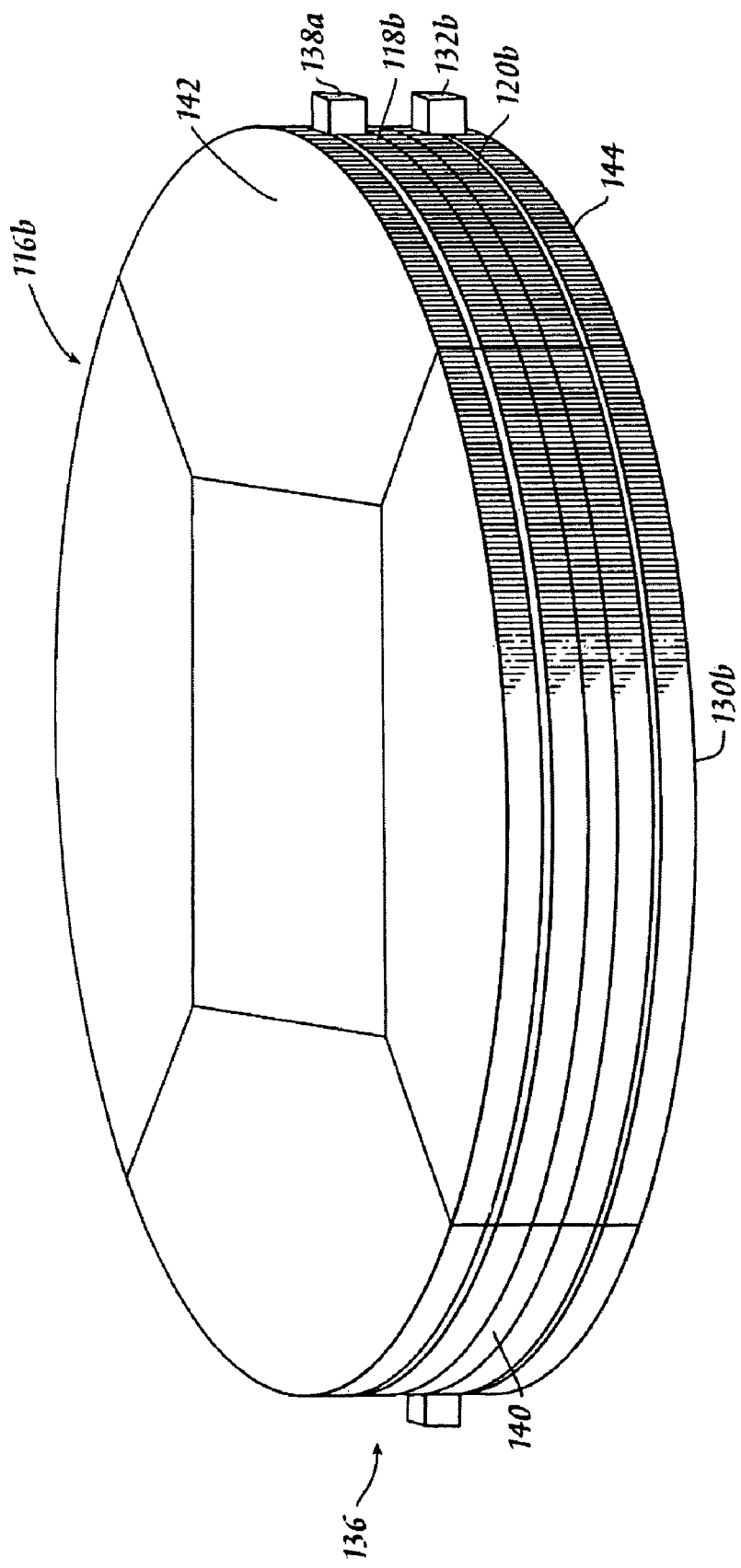
FIG. 15 is a perspective view of another splitter.

FIG. 15 illustrates another splitter 116b having lateral outlets 132b and 138a positioned diametrically opposite inlet 136. It is believed that this inlet-outlet positioning increases separation efficiency of splitter 116 over the positioning shown in FIG. 14, possibly due to reduced dead volume in the flow through splitter 116.

Additional alterations to the chamber are possible to reduce dead flow volume or increase separation efficiency. For example, the various chambers may be configured with an elliptical shape to better channel flow of fluids through splitter 116. Outlet chambers 142 and 144 may similarly be tapered, e.g., from 300 µm height adjacent inlet 136 to 100 µm adjacent outlets 132b and 138a.

In one example, a splitter 116 separates an incoming plug flow of fuel and water into individual single phase streams or flows. A 5-10 mm diameter chamber having a height of 200-400 µm is defined between two membranes 118 and 120, one lipophilic and the other hydrophilic. Reduced chamber diameter increases the average velocity across a given filter area for the same inlet flow rate, increasing the pressure on the filters. The relatively small splitter volume and proximity of filters 118 and 120 allow separation of fluids for testing with as little as 0.5 ml of fuel. This allows the system to be portable for identification, quantification and authentication of liquids in the field. The system may also be modified to be used in continuous flow testing, for example, in quality control during manufacturing to monitor marking and dosing systems. In some cases, such as with markers in LPG, a single extraction may be sufficient to isolate the marker for testing.

Splitter configurations may be selected (e.g., diameter, chamber heights) as a function of desired flushing efficiency, ease and cost of fabrication, the expected filter lifetime and the ease of replacing the filters.

Also, the systems, methods and features may be used in combination with other systems or methods, such as an antibody system. For example, the plug flow system may be used to quickly and initially screen fuels with the antibody test, XRF or GC tests being used to provide further data. In another example, multiple markers are provided in the material to be authenticated and the plug flow system can be used to detect a first marker and another testing system used to detect another marker. Thus, the plug flow system can be used in tandem with other detection systems. Similarly, by detecting different ratios of markers, the plug flow system can by used to detect grade swapping in fuels or to otherwise authenticate materials.

All of the methods disclosed and claimed herein can be made and executed without undue experimentation in light of the present disclosure. It will be apparent to those of skill in the art that variations may be applied to the methods and in the steps or in the sequence of steps of the method described herein without departing from the concept, spirit, and scope of the invention. More specifically, it will be apparent that certain compositions which are chemically related may be substituted for the compositions described herein while the same or similar results would be achieved. All such similar substitutes and modifications apparent to those skilled in the art are deemed to be within the spirit, scope, and concept of the invention as defined by the appended claims.

The invention clamed is:

1. A system comprising:
a plug flow mixer having a first fluid inlet receiving a fluid containing a marker, a second fluid inlet receiving a transfer agent, and an outlet conveying a plug flow of the fluid and transfer agent, wherein the plug flow mixer and the outlet are configured to transfer the marker from the fluid to the transfer agent; and
a splitter having first and second filters separating from the plug flow, the fluid and the transfer agent bearing the marker.

2. The system of claim 1, further comprising a second plug flow mixer having an inlet receiving the first transfer agent bearing the marker, and a second inlet receiving a second transfer agent, and an outlet conveying a plug flow of the first and second transfer agents, wherein the mixer and outlet are configured to transfer the marker from the first transfer agent to the second transfer agent.

3. The system of claim 1, further comprising a detector in communication with an outlet of the splitter detecting the presence of the marker in the transfer agent.

4. The system of claim 1, wherein the splitter comprises a first filter and a second filter, the filters configured respectively to selectively pass one of the fluid and the transfer agent and to substantially block the other of the fluid and the transfer agent.

5. The system of claim 4, wherein the first filter is a lipophobic membrane and the second filter is a hydrophobic membrane.

6. The system of claim 5, wherein the first and second filters are spaced apart a distance approximately equal to a diameter of the outlet of the plug flow mixer, whereby plugs conveyed from the outlet are in contact with both the first and the second filter within the splitter.

7. The system of claim 4, wherein the splitter further comprises:
a splitter inlet receiving a plug flow into a filter chamber defined in part by the first and second filters;
a first outlet chamber and first outlet conveying the fluid passed by the first filter;
a second outlet chamber and second outlet conveying the transfer agent passed by the second filter.

8. The system of claim 7, wherein one of the first and second outlet chambers is positioned diametrically opposite the splitter inlet.

9. The system of claim 7, wherein one of the first and second outlet chambers is tapered in height or width between the inlet and the outlet.

10. The system of claim 7, wherein the filter channel and first and second outlet channels are configured as an ellipse between the splitter inlet and the outlet chamber outlets.

11. The system of claim 7, wherein the splitter inlet has a diameter of between 5-10 mm, a height of between 200-400 μm and the outlet chambers each have a diameter of between 5-10 mm and a height of between 100-400 μm.

12. The system of claim 7, wherein one of the first and second outlet chambers defines a network of channels conveying one of the fluid and the transfer agent to a respective one of the chamber outlets.

13. The system of claim 1, wherein the fluid comprises a fuel, a lubricant, spirits, or a liquid pharmaceutical.

14. The system of claim 1, wherein plug flow mixer is in a form of a T-junction or Y-junction.

15. A system comprising:
a plug flow mixer having a first fluid inlet for receiving a fluid containing a marker, a second fluid inlet for receiving a transfer agent and an outlet for conveying a plug flow of the fluid and transfer agent, wherein the plug flow mixer and the outlet are configured to permit transfer of the marker from the fluid to the transfer agent; and
a splitter having first and second filters for separating from the plug flow, the fluid and the transfer agent bearing the marker.

16. The system of claim 15, further comprising a second plug flow mixer having an inlet for receiving the first transfer agent bearing the marker and a second inlet for receiving a second transfer agent, and an outlet for conveying a plug flow of the first and second transfer agents, wherein the mixer and outlet are configured to permit transfer of the marker from the first transfer agent to the second transfer agent.

17. The system of claim 15, wherein the splitter comprises a first filter and a second filter, the filters configured respectively to selectively pass one of the fluid and the transfer agent and to substantially block the other of the fluid and the transfer agent.

18. The system of claim 17, wherein the first and second filters are spaced apart a distance approximately equal to a diameter of the outlet of the plug flow mixer, whereby plugs conveyed from the outlet are in contact with both the first and the second filter within the splitter.

19. The system of claim 17, wherein the splitter further comprises:
a splitter inlet for receiving a plug flow into a filter chamber defined in part by the first and second filters;
a first outlet chamber and first outlet for conveying the fluid passed by the first filter;
a second outlet chamber and second outlet for conveying the transfer agent passed by the second filter.

20. The system of claim 19, wherein one of the first and second outlet chambers is positioned diametrically opposite the splitter inlet.

21. The system of claim 19, wherein one of the first and second outlet chambers is tapered in height or width between the inlet and the outlet.

22. The system of claim 19, wherein the filter channel and first and second outlet channels are configured as an ellipse between the splitter inlet and the outlet chamber outlets.

23. The system of claim 19, wherein the inlet chamber has a diameter of between 5-10 mm, a height of between 200-400 μm and the outlet chambers each have a diameter of between 5-10 mm and a height of between 100- 400 μm.

24. The system of claim 15, wherein the fluid comprises a fuel, a lubricant, spirits, or a liquid pharmaceutical.

* * * * *